United States Patent
Fodor et al.

(10) Patent No.: US 9,038,436 B2
(45) Date of Patent: May 26, 2015

(54) FUEL CELL FOR USE IN AN ALCOHOL BREATH TESTER

(71) Applicant: Alcotek, Inc., St. Louis, MO (US)

(72) Inventors: Joe Fodor, Fenton, MO (US); Karl R. Wolf, Jr., Eureka, MO (US)

(73) Assignee: Alcotek, Inc., St. Louis, MO (US)

( * ) Notice: Subject to any disclaimer, the term of this patent is extended or adjusted under 35 U.S.C. 154(b) by 267 days.

(21) Appl. No.: 13/782,652

(22) Filed: Mar. 1, 2013

(65) Prior Publication Data

US 2014/0027281 A1  Jan. 30, 2014

Related U.S. Application Data

(60) Provisional application No. 61/677,081, filed on Jul. 30, 2012.

(51) Int. Cl.
| | |
|---|---|
| *G01N 33/497* | (2006.01) |
| *G01N 27/403* | (2006.01) |
| *G01N 27/404* | (2006.01) |

(52) U.S. Cl.
CPC .......... *G01N 27/403* (2013.01); *G01N 33/4972* (2013.01); *G01N 27/4045* (2013.01)

(58) Field of Classification Search
CPC .......................... G01N 33/497; G01N 33/4972
USPC ................................................. 73/23.3, 31.05
See application file for complete search history.

(56) References Cited

U.S. PATENT DOCUMENTS

| | | | | |
|---|---|---|---|---|
| 3,509,034 A | * | 4/1970 | Harman | 204/412 |
| 3,756,923 A | * | 9/1973 | Dahms | 205/782.5 |
| 3,795,589 A | * | 3/1974 | Dahms | 205/780.5 |
| 4,132,616 A | * | 1/1979 | Tantram et al. | 204/415 |
| 4,487,055 A | | 12/1984 | Wolf | |
| 4,498,970 A | * | 2/1985 | Chand | 204/415 |
| 5,291,898 A | | 3/1994 | Wolf | |
| 5,514,253 A | * | 5/1996 | Davis et al. | 205/782.5 |
| 5,738,773 A | * | 4/1998 | Criddle et al. | 204/411 |
| 5,759,368 A | | 6/1998 | Kuhn | |
| 6,923,040 B2 | | 8/2005 | Stock | |
| 6,967,581 B2 | | 11/2005 | Karsten | |
| 7,855,027 B2 | | 12/2010 | Bayer et al. | |
| 8,161,793 B2 | | 4/2012 | Mitchell | |
| 8,888,978 B2 | * | 11/2014 | Mitchell et al. | 204/431 |
| 2006/0032742 A1 | | 2/2006 | Babes-Dornea et al. | |
| 2008/0009693 A1 | | 1/2008 | Hawthorne et al. | |

(Continued)

FOREIGN PATENT DOCUMENTS

KR  20110029749 A  3/2011

OTHER PUBLICATIONS

International Search Report, International Patent Application No. PCT/US13/51442, mailed on Oct. 16, 2013, 10 pages.
"Alco-Sensor FST Operators Manual," Intoximeters, Inc., http://crwlawyers.com/alco-sensor%20FST%20manual.pdf, Sep. 2004, 29 pages.

(Continued)

*Primary Examiner* — Peter Macchiarolo
*Assistant Examiner* — Nathaniel Kolb
(74) *Attorney, Agent, or Firm* — Lewis Rice LLC

(57) ABSTRACT

An improved alcohol fuel cell sensor and alcohol breath tester assembly where wires for connection to the electrodes are bent to have a generally planar base portion which may be positioned toward the center of the electrodes and an upright that then extends to the outside of the case. The uprights are generally perpendicular to the base allowing the wires to exit the housing toward the center, as opposed to toward an edge.

14 Claims, 8 Drawing Sheets

(56) References Cited

U.S. PATENT DOCUMENTS

| | | |
|---|---|---|
| 2009/0193873 A1* | 8/2009 | Nakamura et al. ........... 73/31.05 |
| 2010/0173215 A1 | 7/2010 | Chou et al. |
| 2012/0174651 A1 | 7/2012 | Mitchell |
| 2012/0228139 A1* | 9/2012 | Mitchell et al. ............... 204/431 |

OTHER PUBLICATIONS

International Search Report, International Patent Application No. PCT/US13/52492, mailed on Oct. 31, 2013, 11 pages.

* cited by examiner

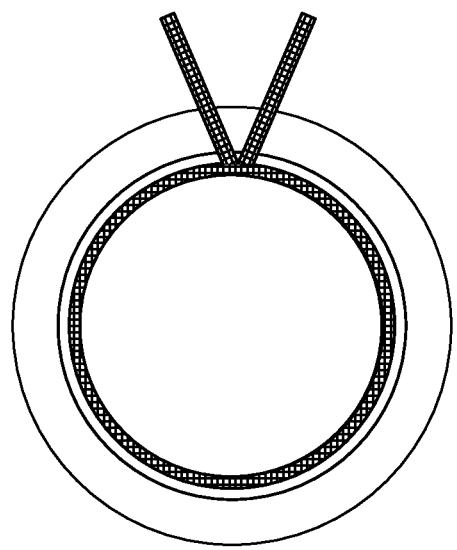
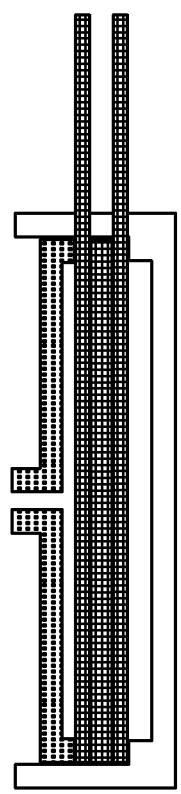
Figure 5
(prior art)

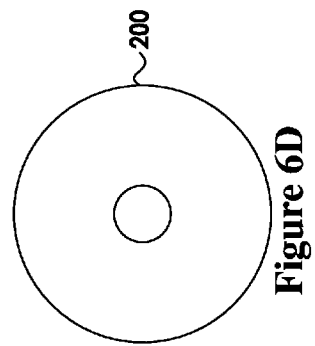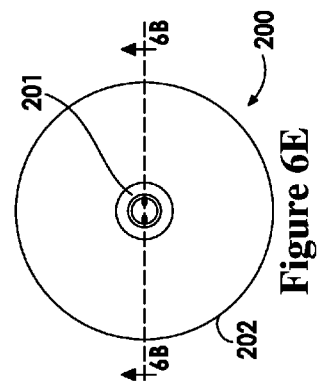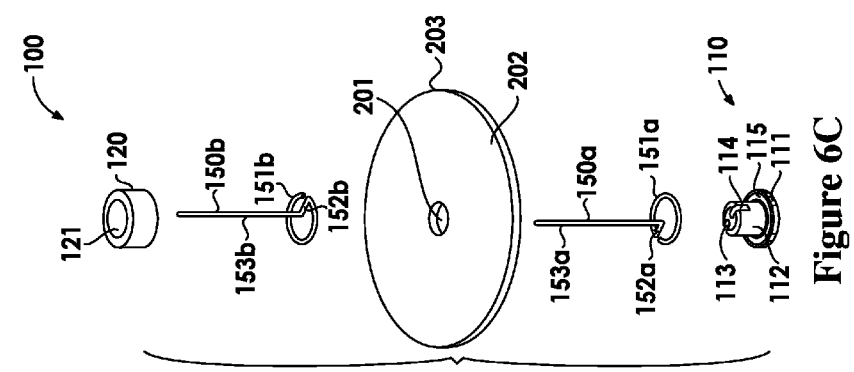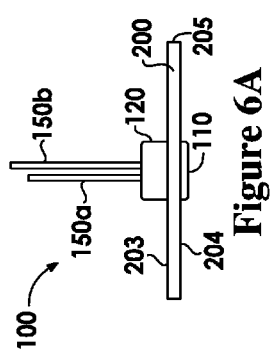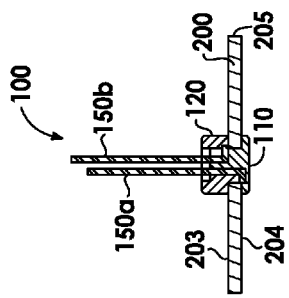

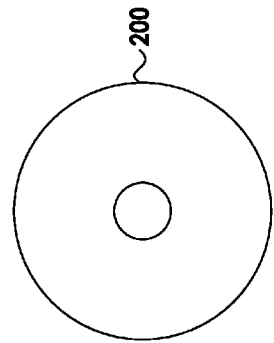
Figure 7D
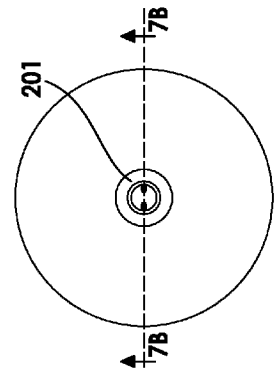
Figure 7E
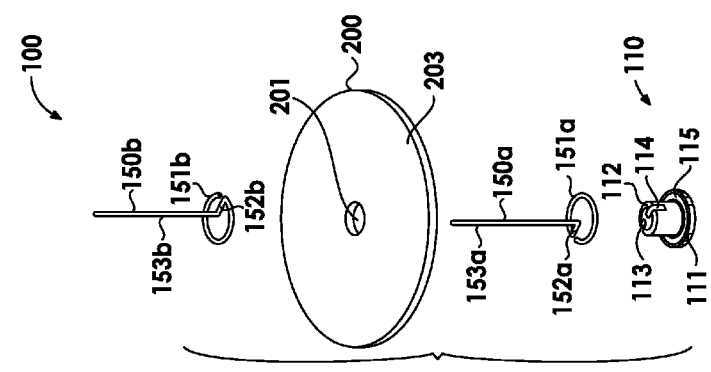
Figure 7C
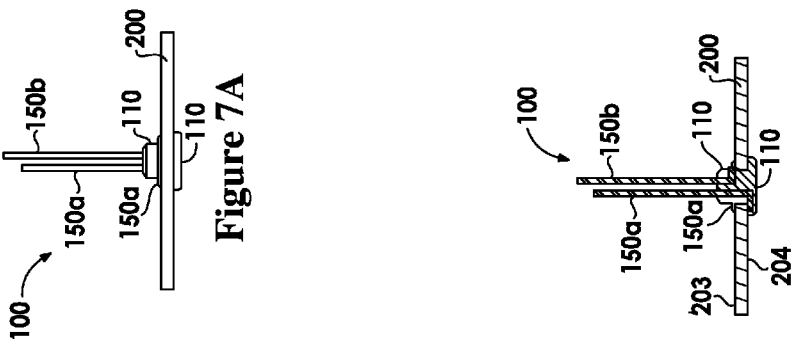
Figure 7A
Figure 7B

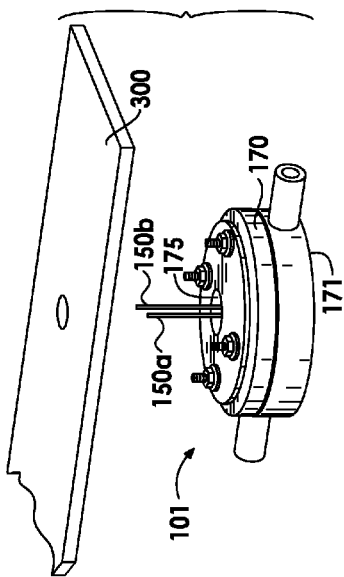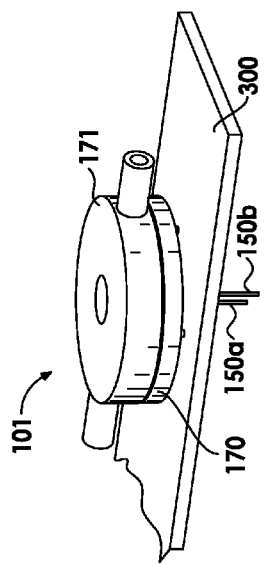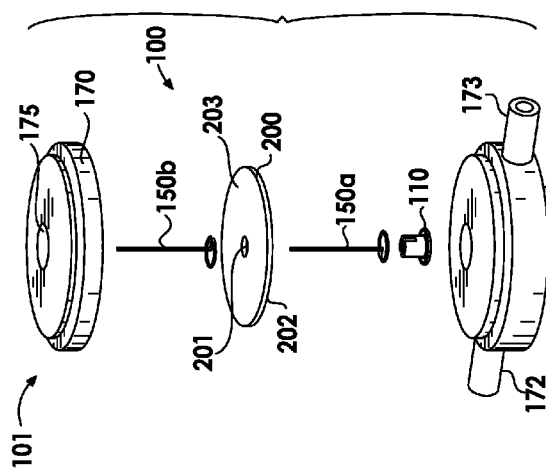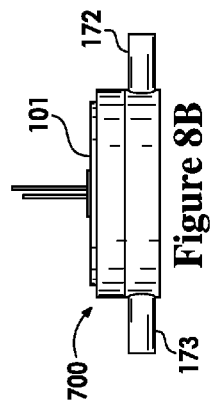

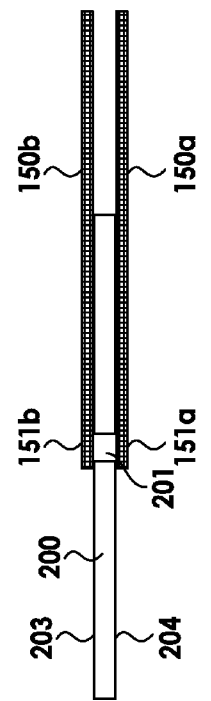
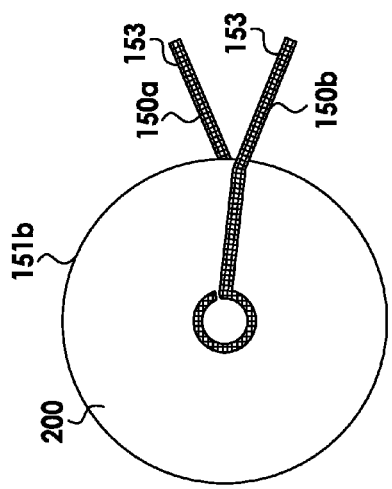
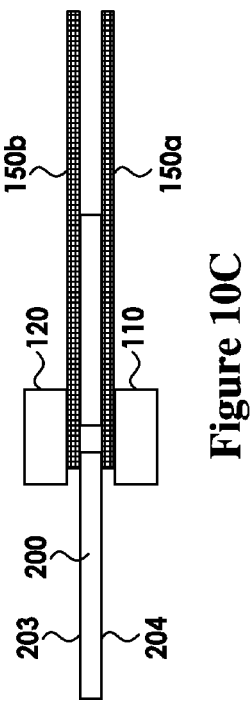
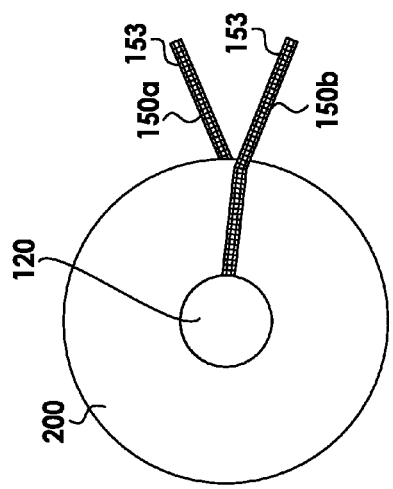

FUEL CELL FOR USE IN AN ALCOHOL BREATH TESTER

CROSS REFERENCE TO RELATED APPLICATION(S)

This application claims the benefit of U.S. Provisional Patent Application Ser. No. 61/677,081, filed Jul. 30, 2012, the entire disclosure of which is herein incorporated by reference.

BACKGROUND

1. Field of the Invention

This disclosure relates generally to devices for estimating blood alcohol content from a breath sample, and more particularly, to fuel cells for use in estimating blood alcohol content from a breath sample.

2. Description of the Related Art

An alcoholic beverage is a drink containing ethanol, commonly known as alcohol, although in chemistry the definition of alcohol includes many other compounds. Alcohol, specifically ethanol, is a psychoactive drug and is a powerful central nervous system depressant with a range of side effects.

Alcohol has a biphasic effect on the body, which is to say that its effects change over time. In the initial stages of intoxication, alcohol generally produces feelings of relaxation and cheerfulness. Further consumption however affects the brain leading to slurred speech, blurred vision, clumsiness and delayed reflexes, among other coordination problems. This condition is commonly referred to as intoxication or drunkenness, and eventually subsides when the alcohol has fully metabolized in the body.

When a human drinks alcohol, the alcohol housed in the stomach passes into the bloodstream. Cell membranes are highly permeable to alcohol, so once alcohol is in the bloodstream it can diffuse into nearly every biological tissue of the body. Once in the bloodstream, the alcohol circulates to the brain, resulting in intoxication, loss of inhibition and impairment of motor skills such as driving a vehicle. The amount of alcohol consumed and the circumstances surrounding consumption play a large role in determining the extent of an individual's intoxication. Examples of such circumstances include the amount of food in the stomach at the time of alcohol consumption and the hydration level of the individual at the time of consumption, among others.

Due to the coordination impairment and other symptoms associated with intoxication and drunkenness, most countries have laws against drunk driving, i.e., driving with a certain concentration of ethanol in the blood. The legal threshold of blood alcohol content ranges from 0.0% to 0.08%, depending on the jurisdiction. Punishments for operating a vehicle over the legal limit in a given jurisdiction generally include fines, temporary loss of an individual's driving license and imprisonment. Creation of these laws has led to a market for devices to accurately measure the blood alcohol content of individuals operating motor vehicles.

Blood alcohol content (BAC) or blood alcohol concentration is the concentration of alcohol in the blood (weight per unit volume). While blood alcohol content can be directly measured in a hospital laboratory setting, it is more common for it to be measured in law enforcement situations by estimation from an individual's breath alcohol concentration using a breath alcohol testing machine.

In the world of alcohol-breath testing and related fields of alcohol testing, one of the most common configurations uses fuel cells as alcohol sensors, with the assembly allowing breath, air, gas, or vapor to be passed into the fuel cell. In its simplest form, the alcohol fuel cell is a wafer consisting of a chemically inert porous material coated on both sides with thin layers of catalyst such as platinum (forming upper and lower platinum electrode layers.) The porous material sandwiched between the two platinum layers contains a liquid acid-electrolyte. The electrolyte allows charges to move between the two electrode layers of the wafer. Those skilled in the art would understand that the chemically inert porous material, filled with a liquid acid-electrolyte, could be replaced by, under certain circumstances, a solid electrolyte element.

Round, platinum wire electrical connections are then applied to the platinum electrodes and connected to an external circuit. In this regard, the wafer is generally a solid, planar shape allowing for wire to electrode connections at any point on the wafer. The entire fuel cell sensor is mounted in a plastic case, which is provided with a gas inlet that allows a breath sample to be introduced into the assembly. The basic configuration is as described above, and illustrated in FIG. 1.

In the fuel cell sensor, the top platinum electrode (the one closest to the gas inlet) oxidizes any alcohol in the breath sample to produce acetic acid in a 2 step process (ethanol→acetaldehyde→acetic acid) and which also produces free electrons in the process. Hydrogen ions (H+) are also freed in the process, and migrate to the lower platinum electrode of the cell, where they combine with atmospheric oxygen to form water, resulting in a deficiency of electrons on the lower electrode equal to the excess of electrons produced on the upper surface. Because the two electrode surfaces are connected electrically, a current flows through this external circuit to neutralize the charge. With suitable amplification, this current is a precise indicator of the amount of alcohol consumed by the fuel cell, as the number of electrons produced is directly and linearly proportional to the number of alcohol molecules arriving at the catalyst surface. With the number of alcohol molecules, the blood alcohol content can then be determined. This process is illustrated in FIG. 2.

For the fuel cell sensor to operate properly, the wires connecting the electrodes must have a low ohm connection with the platinum electrodes on the wafer. Otherwise, a high resistance connection hinders the operation of the fuel cell and makes it less accurate and slower. The "wires" can take on a variety of forms, but as noted above, round, solid platinum wires are the most common. They are generally considered the best, most readily available, and most versatile. Other forms can be used besides round wire, such as wire mesh or flat ribbon. Additionally, other materials can be used besides platinum, such as gold or plated materials, but resistance to the harsh acidic environment of a fuel cell can limit the number of choices of conductors. In any event, the wire should not disrupt the thin layer of platinum, and should take into consideration the well understood effects of dissimilar metal junctions.

As noted herein, it is common practice by those skilled in the art to use small round platinum wires. platinum, however, is an expensive commodity, so using as little wire as possible can be important economically. The platinum wire only needs to contact a portion of the platinum surface. Thus, at times, the platinum wires are transitioned to some other, more economical conductor once the wires have exited the harsh acidic environment inside the fuel cell case/assembly.

Moreover, there exists a considerable price pressure in the marketplace for alcohol fuel cell sensors, specifically in the breath-testing field. Most manufacturers use low cost and simple components in the construction of such fuel cell sensor assemblies. Added complexity of design can result in higher costs for tooling, parts, and labor. For all these reasons, a common simple construction assembly used by many manufacturers can be generally described as follows and as illustrated in FIG. 3: a first wire (a) is added to a lower plastic case (b); a platinum coated disk (c) is added on top of the first wire (a) and case (b); a second wire (d) is added over the disk (c); and a upper plastic cover (e) is added to seal the assembly.

It is important that the assembly be sealed for a couple of reasons. First, it ensures that no electrolyte can leak out of the assembly. Second, gas can only enter the assembly through the inlet. For sealing, manufacturers use glues, epoxies, ultrasonic welding, flexible seals, and other types of sealing methods known to those skilled in the art. In order for the assembly to be fully sealed, the case halves must be sealed together, the wires must be sealed to the case, and the periphery of the disk must be sealed to the inside of the case half.

Importantly, the wires must have good contact with the platinum surface of the electrodes. This contact is most easily accomplished by a clamping force that "squeezes" the platinum disk between the wires—often the platinum wires can actually compress the platinum electrodes and embed in that surface to some degree. Additionally, this contact and force needs to be maintained throughout the life of the sensor.

As shown in FIG. 3, with many of the prior art assemblies, as the wires are added to the assembly, some of the parts in the assembly become canted. Not only does this make the assembly more difficult, but the wires may lose contact with the platinum electrode surface over time, resulting in non-functionality of the fuel cell.

There have been attempts in the prior art to ensure this contact, but they all have their own problems. As shown in FIG. 4, one option is to add spacers or compensating elements in areas where the wires are not present. This design, however, is much more complicated and requires a critical equivalence between the dimensions of the compensating elements and the platinum wire in order to properly function. Additionally, this design results in difficulties in maintaining the same clamping force across a batch of assemblies, with some of the manufactured assemblies inevitably clamping the platinum wire to the electrode surface better than others. Although the compensating elements could be spring-loaded in some form to improve the design to ensure proper and even clamping force, such spring-loading only complicates the assembly even further.

A second option is to shape the wires into loops (or portions of loops) that encircle the circumference of the wafer or to span the entire length or diameter of the wafer, as shown in FIG. 5. This is a more reliable option (if used with the proper clamping force) in that it provides more assurance that the platinum wire will remain in contact with the electrode surface, as the housing clamps the outside of the wafer and locks the wires into place. However, the circumferential loops and/or lengthened wire require much more platinum wire which adds significant expense to the assembly.

In summary, fuel cell assemblies generally require some type of wire (e.g., platinum wire) to be attached to platinum electrodes in a secure, low resistance manner. One type of assembly uses a permanent clamping force to hold the electrodes and wires in close electrical contact, with the expensive wires generally spanning nearly the entire length, diameter, or circumference of the wafer. The other requirements of the assembly (such as simplicity of parts, sealing, low cost, and ease of assembly), however, can result in a design with significant risk in the reliability of the internal electrical connection. The largest risk is that a less than optimal electrical connection made during the assembly process may only manifest itself later during field use, resulting in a non-functional breath tester.

SUMMARY

In view of the above described and other problems in the art, disclosed herein is an improved alcohol fuel cell sensor and alcohol breath tester assembly where wires for connection to the electrodes are bent to have a generally planar base portion which may be positioned toward the center of the electrodes and an upright that then extends to the outside of the case. The uprights are generally perpendicular to the base allowing the wires to exit the housing toward the center, as opposed to toward an edge. The resultant assembly incorporates a contact force between the wires and platinum electrode while insuring an electrical contact between the platinum electrode and wires that last over a significant period of time. This results in a design that is reliable in the field. Further, the disclosed cell does this by means independent of other assembly steps required to make a complete alcohol breath tester assembly, and by using minimum amounts of platinum wire, resulting in a less expensive yet reliable fuel cell.

The disclosed fuel cell sensor and assembly can have further advantages over the state of the art: (1) it can be easily incorporated into a vast variety of independent housing designs that otherwise need not address the integrity of the internal electrical connection; (2) it is scalable, and, thus, not restricted to any particular size or shape of fuel cell; (3) the fuel cell may be incorporated as an independent sub-assembly or in concert with the fuel cell case in some customized manner; (4) the fuel cell can be very simply incorporated into a printed circuit board assembly in a robust and economical manner; (5) the fuel cell allows for incorporation of a second wafer (such as an electrolyte reservoir wafer).

There is described herein, among other things, a fuel cell sensor comprising: a generally flat wafer having: two opposing major surfaces; and an electrode on each of the two opposing major surfaces; the electrode extending to an outer periphery; and a plurality of elongated wires having a major dimension, each of the wires including: a base portion; and an upright; wherein the base portion is arranged to be all of the following: non-linear in the major dimension; generally planar within a perimeter; and the perimeter being smaller than the outer periphery; and wherein the upright is generally linear in the major dimension; wherein the base portion of a first of the plurality of elongated wires is arranged parallel to and in contact with a first of the electrodes; and wherein the base portion of a second of the plurality of elongated wires is arranged parallel to and in contact with a second of the electrodes.

In an embodiment of the fuel cell, the generally flat wafer includes a hole.

In an embodiment of the fuel cell, the base portion and the upright are arranged so that the upright is generally orthogonal to the plane of the base portion.

In an embodiment of the fuel cell, the upright of the first of the plurality of elongated wires extends through the hole and the upright of the second of the plurality of elongated wires is above the hole.

In an embodiment the fuel cell further comprises a clamping pin, the clamping pin including: a pin base, the pin base being adjacent to the base portion of the first of the elongated wires; and a column, the column extending through the hole.

In an embodiment of the fuel cell, the column further includes: a first groove through which the upright of the first of the plurality of elongated wires extends; and a second groove through which the upright of the second of the plurality of elongated wires extends.

In an embodiment of the fuel cell, the base further includes a groove corresponding to the base portion of the first of the elongated wires.

In an embodiment the fuel cell further comprises a sleeve, the sleeve including a central opening corresponding in size and shape to the column so that the sleeve can fit over the column.

In an embodiment of the fuel cell, the sleeve includes a geometric tab feature, the geometric tab feature mating with the slot on the clamping pin.

In an embodiment of the fuel cell, the hole passes through the center of the electrodes.

In an embodiment of the fuel cell, the fuel cell is enclosed in a housing having an upper portion and a lower portion, the upper portion including a central hole, and both the upright of the first of the plurality of elongated wires and the upright of the second of the plurality of elongated wires extend through the hole in the upper portion.

In an embodiment of the fuel cell, the base portion of the first of the plurality of elongated wires is closer to the lower portion than the upper portion and the base of the second of the plurality of elongated wires is closer to the upper portion than the lower portion.

In an embodiment of the fuel cell, a gas sample is supplied through a gas intake port in the lower portion.

In an embodiment of the fuel cell, the electrodes comprise platinum.

In an embodiment of the fuel cell, the wires comprise platinum.

In an embodiment of the fuel cell, the wires are selected from the group consisting of: round wires and wire ribbons.

In an embodiment of the fuel cell, the base portion and the upright are arranged so that the upright is generally co-planar to the plane of the base portion.

There is also described herein, a fuel cell sensor comprising: a generally flat wafer having: two opposing major surfaces; and an electrode on each of the two opposing major surfaces the electrode extending to an outer periphery; and a plurality of flex circuits, each of the flex circuits including: a generally planar base portion having a perimeter; and an upright; wherein the perimeter is smaller than the outer periphery; and wherein the upright extends generally linearly from the base portion; wherein the base portion of a first of the plurality of flex circuits is arranged parallel to and in contact with a first of the electrodes; and wherein the base portion of a second of the plurality of flex circuits is arranged parallel to and in contact with a second of the electrodes.

In an embodiment of the fuel cell, the plurality of flex circuits include selective gold plating on all or part of the planar portion, such plating providing an electrical connection to the electrode.

In an embodiment of the fuel cell, the plurality of flex circuits include selective gold plating; such plating being thicker than the remainder of the flex circuit.

In an embodiment of the fuel cell, the plurality of flex circuits have at least a portion which is acid-resistant.

BRIEF DESCRIPTION OF THE DRAWINGS

FIG. 5 depicts the assembly of FIG. 3 with the wires shaped in large loops around the periphery of the wafer to correct the canted nature of the assembly.

FIG. 6A is a side view of an embodiment of a fuel cell with a sleeve being utilized.

FIG. 6B is a cross-sectional side view of the embodiment of FIG. 6A.

FIG. 6C is a perspective view of the fuel cell of FIG. 6A.

FIG. 6D is a bottom view of the fuel cell of FIG. 6A.

FIG. 6E is a top view of the fuel cell of FIG. 6A.

FIG. 7A is a side view of an embodiment of a fuel cell without a sleeve being utilized.

FIG. 7B is a cross-sectional side view of the embodiment of FIG. 7A.

FIG. 7C is a perspective view of the embodiment of FIG. 7A.

FIG. 7D is a bottom view of the fuel cell of FIG. 7A.

FIG. 7E is a top view of the fuel cell of FIG. 7A.

FIG. 8A is an exploded a perspective view of an embodiment of an assembly with the fuel cell shown in FIG. 7C combined with a lower housing and upper housing.

FIG. 8B is a side view of the embodiment of FIG. 8A.

FIG. 9A is a top perspective view of the embodiment of FIG. 8, with the assembly being connected to a circuit board.

FIG. 9B is a bottom perspective view of the embodiment of FIG. 9A.

FIG. 10A is a side view of an embodiment of a fuel cell where the centrally clamped wires exit the fuel cell in the conventional manner on the side.

FIG. 10B is a top down view of the embodiment of FIG. 10A.

FIG. 10C is a side view of the embodiment of FIG. 10A with the clamping pin and sleeve in place.

FIG. 10D is a top down view of the embodiment of FIG. 10C.

DESCRIPTION OF PREFERRED EMBODIMENT(S)

Figure 1:
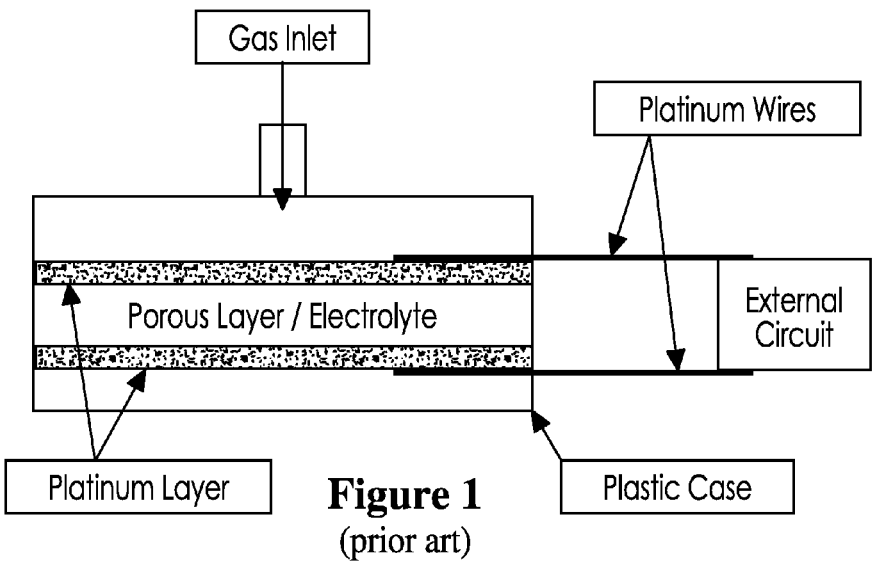
FIG. 1 depicts a basic configuration of an embodiment of a fuel cell sensor and assembly of the prior art.
Figure 2:
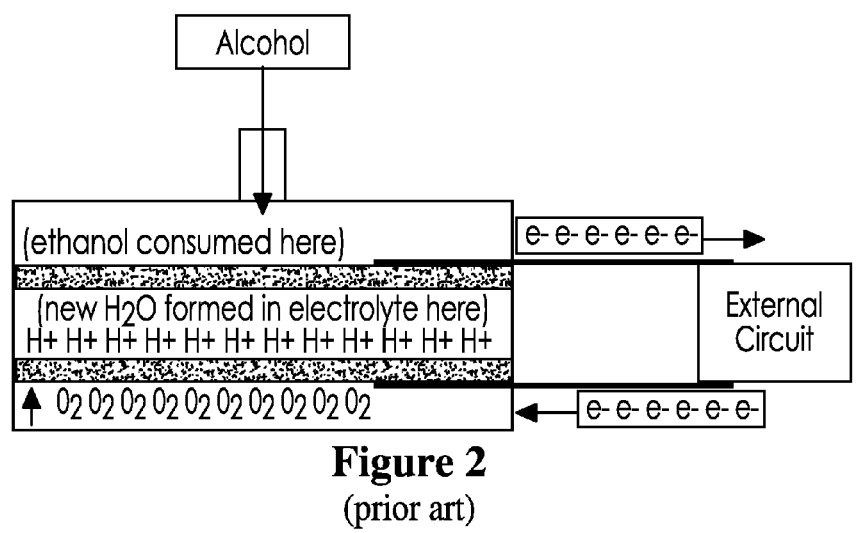
FIG. 2 depicts the embodiment of FIG. 1 and showing the chemical reaction and current flow as alcohol from a breath sample is introduced into the assembly.

Turning now to FIGS. 6-9, the disclosed fuel cell (100), and resultant assembly (101), will be described in greater detail. Generally, the fuel cell (100) will comprise a platinum wafer (200), a clamping pin (110), and two wires (150). As discussed more fully below, the wafer (200) is similar to the prior art wafers excepting that the wafer (200) has an interior hole (201) within which the clamping pin (110) is mounted, with the clamping pin (110) housing the wires and creating a permanent force for connecting the wires (150) to the wafer (200).

With the interior hole (201) and the clamping pin (110), it is not necessary, as in the prior art, for the wires (150) to span the length or diameter of the wafer (200) or for the wires (150) to exit on the side of the wafer (200). Instead, the wires (150) are able connect to and extend from the wafer (200) at or near the center of the wafer (200). The fuel cell (100) can then be enclosed in various types of housing (700) with the wires (150) positioned towards the center (as opposed to the periphery) of the housing (700) while still maintaining sufficient contact with the wafer (200). An example is a case (700) that creates an alcohol breath tester assembly (101) which allows gas/breath to enter the assembly (101) through a gas intake port (173).

As noted above, the wafer (200), or a combination of wafers, generally comprises a chemically inert center material (205) such as, but not limited to, Polyvinyl Chloride or Polypropylene coated on both sides to a periphery (202) at or around the outside edge of the inert center material (205) with thin layers of platinum (forming upper and lower platinum electrode layers (203) and (204)). An acid-electrolyte material such as sulfuric or phosphoric acid fills the pores of the inert center layer (205) sandwiched between the two electrode layers (203) and (204). The electrolyte allows charges to move between the two electrode layers (203) and (204). The wafer (200) generally has a defined shape as well as a defined hole (201) away from the periphery (202) and generally in the center of the wafer (200). The wafer (200) can be any shape, including, for example, triangles, rectangles, squares, trapezoids, hexagons, ovals, and the like. A preferred embodiment is a round electrode wafer (200) with a round, central hole (201) as shown in FIGS. 6 and 7.

As noted above, wires (150) are applied to both electrodes (203) and (204) of the wafer (200) in order to connect with an external circuit. One wire (150b) is securely applied to the upper electrode layer (203) and the other wire (150a) is securely applied to the lower electrode layer (204). Although by no means necessary, a preferred embodiment uses two wires (150) of substantially identical design and length to simplify electrical connections. Thus, components of each wire (150a) and (150b) are referred to together in this disclosure without use of a letter when logical to refer to features common to both with the letter "a" being used to refer to components of the lower wire (150a) when appropriate and the letter "b" being used to refer to components of the upper wire (150b) when appropriate.

The wires (150) are generally elongated round, platinum wires, although other suitable metals could be utilized, including, for example, gold or plated materials, and other types could be utilized, including, for example, wire mesh or flat ribbon. Further, the wires may be replaced by flex circuits (651) as shown in FIG. 11 or by other structures having similar shape as understood by those of ordinary skill.

The wires (150) are generally bent and configured such that they comprise a base portion (151) where the wire (150) is bent to be a non-linear but generally planar shape (e.g. a polygon or circle) and having a perimeter smaller than the periphery (202) of the wafer (200) but no smaller than the exterior dimension of the hole (201). The wires (150) also comprise a leg (152) extending inward toward the center of the base portion (151) and along the same plane as the base portion (151), and an upright (153). In the embodiment of FIGS. 6-9, the upright (153) extends substantially perpendicular to the base portion (151) and leg (152). In the embodiment of FIGS. 10 and 11, the upright extends generally coplanar with the base portion (151) The base portion (151b) and leg (152b) of the wire (150b) are the parts applied in electrical contact with the upper platinum layer (203), with the base portion (151a) and leg (152a) of the wire (150a) being applied in electrical contact with and the lower platinum layer (204). The clamping pin (110) then securely holds the wire (150a) in place on the wafer (200) with the clamping pin (110), a sleeve (120), and/or the upper housing (170) holding the wire (150b) in place, as discussed below.

Because the base portion (151) stays clear of the periphery (202) of the electrode (203) or (204) and is generally around the center of the wafer (200), a smaller amount of wire (150) (and, thus, platinum when platinum is used) is required than designs which cross the wafer (200) or surround the electrode (203) or (204) toward the periphery (202) (such as that shown in FIG. 5). Additionally, a variety of case (700) designs can be utilized to easily seal the wafer (200) around its edges in the resultant assembly (101), for example, the upper housing (170) and lower housing (171) shown in FIG. 8 and discussed below.

As noted above, the clamping pin (110) secures the wires (150) to the wafer (200) and ensures that an electrical connection is maintained. As such, the clamping pin (110) is generally securely mounted in and about the interior hole (201) of the electrode wafer (201), as shown in FIGS. 6 and 7. In an embodiment, the clamping pin (110) comprises a pin base (111) and a column (112) extending from the center of the pin base (111). The base may include a groove (115) between the outside of the pin base (111) and the column (112), with the groove (115) sized and shaped for receiving the base portion (151a) of one of the wires (150a), as discussed below. In the depicted embodiment, both the pin base (111) and column (112) are circular to match the shape of the hole (201) in the wafer (200) with the outer diameter of the column (112) approximately equal to the inner diameter of the wafer hole (201) in order to securely and snugly mount the pin (110) in the hole (201).

As noted above, however, the hole (201) and wafer (200) may be any shape, and as a result, the column (112) and pin base (111) similarly may be any shape and will generally be a complimentary shape to the hole (201). Regardless of the shape, the pin (110) is generally able to be securely placed into the hole (201) in the wafer (200), which allows the wires (150) to be securely and permanently connected to the wafer (200). In other words, a case or housing (700) is not required to insure the integrity of the electrical connection between the wires (150) and the wafer (200) and the fuel cell sensor (100) may be installed in nearly any case design. One means for accomplishing this secure connection is to have the column (112) and hole (201) approximately the same size and shape, although this is by no means the only way to have the pin (110) securely placed into the hole (201).

In addition to the groove (115) for receiving the wire (150a) on the complementary side of the wafer (200), the column (112) of the pin (110) will generally also have two slots (113) and (114) for receiving the two wires (150a) and (150b), respectively. The first slot (113) will generally extend the length of the column (112) such that the slot (113) meets with the groove (115) in order to receive the first wire (150a). The second slot (114) will generally only extend part of the length of the column (112), as the second wire (150b) will be separated from the groove (115) by the wafer (200). In any event, the three receiving parts of the clamping pin (110)—the groove (115) and two slots (113) and (114)—generally receive the wires (150) in such a manner that the wires (150) are securely and snugly connected to the pin (110).

The fuel cell (100) may also include a sleeve (120) for further securing the clamping pin (110), and thus the wires (150), to the wafer (200), as shown in FIGS. 6A-6C. The sleeve (120) is generally a hollow tubular-like structure with the interior passageway sized and shaped to match the column (112) of the clamping pin (110). As a result, the sleeve (120) and clamping pin (110) can be held together by slip fit, press fit, and/or snap fit. Additionally, or alternatively, those skilled in the art would understand that any variety of methods can be used to hold the two pieces together, including, but not limited to, glue, heat weld, or ultrasonic weld. The sleeve (120) can serve to make a similar flanged structure to the pin base (111) on the opposing side of the wafer (200) (at electrode (203)) resulting in a similar clamping structure to both base portions (151) on both wires (150).

The sleeve (120) may also has a geometric tab feature (121) that applies when the pin (110) assembly is installed. This tab feature (121) mates with the slot (113) on the clamping pin (110). This tab feature (121) may act as a barrier to electrically isolate the section of wire (153) from the top platinum layer (203) of the wafer (200) and/or to lock the sleeve (120) and clamping pin (110) together.

As noted, the sleeve (120) is by no means necessary and the wires (150) may be connected with the wafer (200) by merely the clamping pin (110) alone, as shown in FIGS. 7A-7C. Additionally, the sleeve (120) may be incorporated into the upper housing (170) of the assembly (101) to further secure the wires (150) to the wafer (200), as suggested in FIG. 8. Although a particular case (700) design (i.e., the upper and lower housings (170) and (171)) is depicted in FIG. 8, those skilled in the art would readily understand that a variety of case (700) designs could incorporate the sleeve (120) if desired or needed.

As noted throughout, the fuel cell sensor (100) is enclosed or mounted in some type of case (700) (e.g., a plastic case) to form an assembly (101), with the case being provided with a gas inlet (173) that allows a breath sample to be introduced into the assembly. Advantageously, the fuel cell (100) design allows for use in virtually any type of case (700). As depicted in the embodiment of FIGS. 8-9, the case (700) comprises an upper housing (170) with an outlet (175) for the wires (150) and a lower housing (171) with a gas intake port (173) for the breath sample and an optional exhaust port (172) for a mechanical means to move the gas/breath through the fuel cell sensor (100).

The upper housing (170) and a lower housing (171) are then sealed together to form the case (700) and, in conjunction with the enclosed fuel cell (200), a fuel cell assembly (101). The sealing ensures that no electrolyte can leak out of the assembly (101) and that gas can only enter the assembly (101) through the gas intake port (173). For sealing, glues, epoxies, ultrasonic welding, flexible seals, press (friction) fits, and other types of sealing methods known to those skilled in the art can be utilized.

Regardless of the type of case (700) utilized and whether or not the sleeve (120) is utilized, due to the hole (201) in the wafer (200), both wires (150) can exit on the same side of the fuel cell (100) and assembly (101) for easier attachment to, for example, a circuit board (300) or any type of external circuit, and even though the wires (150) each attach to a different side of the wafer (200). Moreover, the attachment to the circuit board (300), or any type of external circuit, can be accomplished with extremely short wires as the wires (150) extend perpendicular to the wafer (200) rather than parallel therewith.

As discussed above, the circuit creates a current within the fuel cell (100) which allows electrons to flow between the upper platinum electrode layer (203) and the lower platinum electrode layer (204). Additionally, with suitable amplification in the external circuit, the current can be used to determine the amount of alcohol consumed by the fuel cell (100), as the number of electrons produced is directly and linearly proportional to the number of alcohol molecules arriving at the catalyst surface.

The fuel cell assembly (101) is generally constructed as follows. First, the base portion (151a) of the first wire (150a) is placed in groove (115) of the pin base (111) of the clamping pin (110) with the upright (153a) and leg (152a) of the first wire (150a) being securely placed in the first slot (113). Second, the first wire (150a) and clamping pin (110) are secured into the hole (201) of the wafer (200) such that base portion (151a) of the first wire (150a) connects with the lower platinum electrode layer (204) of the wafer (200) with the upright (153a) of the first wire (150a) extending through the hole (201). Third, the upright (153b) and leg (152b) of the second wire (150b) are securely placed into the second slot (114) of the clamping pin (110) such that base (152b) of the second wire (150b) connects with the upper platinum electrode layer (203) of the wafer (200) and the upright (153b) of the second wire (150b) extends substantially parallel to the first wire (150a) and is over the hole (201). Finally, the sleeve (120) may optionally be secured over the clamping pin (110), with the tab feature (121) mating with the first slot (113). A groove in the sleeve (120) may also enclose the base (151b).

Next, the upper housing (170) is placed over the fuel cell (100) on the side of the upper platinum electrode layer (203) of the wafer (200), with the wires (150) extending through the outlet (175) of the upper housing (170). The lower housing (171) is then placed over the fuel cell on the side of the lower platinum electrode layer (204) of the wafer (200) and the lower housing (171) and the upper housing (170) are sealed together. It will further be appreciated that the outlet (175) of the upper housing (170) merely allows the wires (150) to pass therethrough but a seal remains such that gas can only enter through the gas intake port (173) and electrolyte cannot leak out of the outlet (175). It should be noted that the case (700) shown in FIG. 8 includes features of a housing such as that discussed in U.S. patent application Ser. No. 13/778,786, the entire disclosure of which is herein incorporated by reference. This arrangement of case (700) can be particularly beneficial with a fuel cell (100) including centrally discharging wires (151) as the wire (151 a) does not intersect as much of the gas chamber supplying the sample to the wafer (200) in such a housing.

As shown in FIG. 10, in the event that the use of centrally exiting wires as shown in FIGS. 6 and 7 is problematic for the fuel cell (100) case (700) being used, the arrangement of using a base portion (151) inside the periphery of the electrode (203) and (204) may be applied to a wafer (200) to help improve connection to the wafer (200), but the manner of the uprights (153) leaving the wafer (200) may be conventional. In the embodiment of FIG. 10, the wires (150) contain base portions (151) with a perimeter around the central hole (201) of the wafer (200). As the hole (201) is not used for the uprights (153) the hole may not be present in an alternative embodiment and the perimeter of the base portions (151) may simply surround the center of the electrodes (203) and (204).

Figure 3:
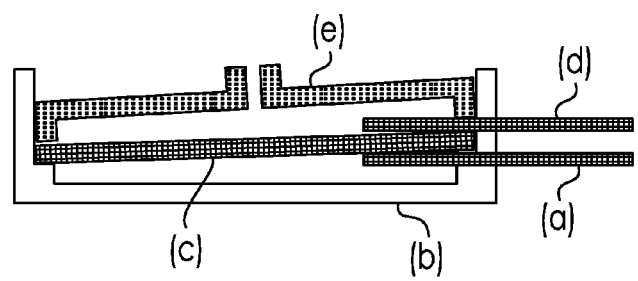
FIG. 3 depicts the canted nature of the assembly and fuel cell that commonly results from the basic configuration of the prior art.
Figure 4:
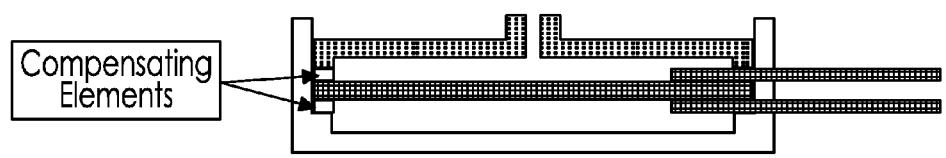
FIG. 4 depicts the assembly of FIG. 3 with compensating elements added to correct the canted nature of the assembly.

The uprights (153) in FIG. 10 extend generally parallel to the plane of the electrodes (203) and (204) and exit the fuel cell housing out the side instead of through the central hole (201). This example takes advantage of the small central clamping area and the use of clamping pin (110) and sleeve (120) to eliminate a need for spacers and provide good electrical connection between wire (150) and electrode (203) and (204). Further, it will provide an assembly where none of the components are generally canted avoiding the problem of FIG. 3.

FIG. 11 provides a still further embodiment to that of FIG. 10 (or with that of FIGS. 6-7) but the coil (150) is replaced with a flex circuit (651). The portion of the flex circuit (651) inside the fuel cell housing will generally be acid-resistant to resist degradation from the environment. This can be accomplished by use of such materials such as, but not limited to, platinum, gold or a polymide such as, but not limited to, poly(4,4'-oxydiphenylene-pyromellitimide) which is available under the trademark Kapton®.

Figure 11A:
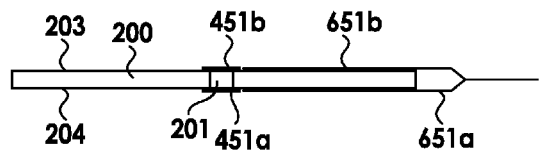
FIG. 11A is a side view of a fuel cell embodiment where the centrally clamped wires are replaced with a flexible circuit.
Figure 11B:
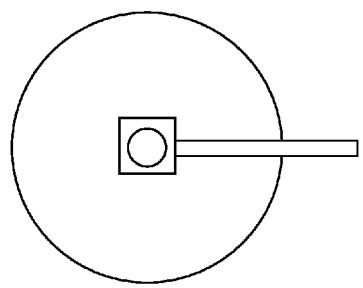
FIG. 11B is a top down view of the embodiment of FIG. 11A.
Figure 11C:
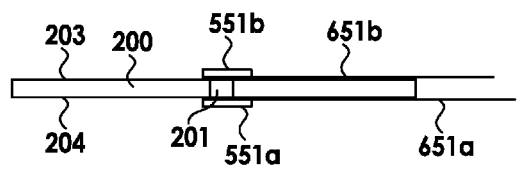
FIG. 11C is a side view of a fuel cell embodiment where the centrally clamped wires are replaced with a flexible circuit that is thicker than the embodiment of FIG. 11A.
Figure 11D:
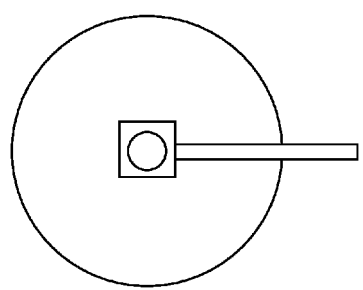
FIG. 11D is a top down view of the embodiment of FIG. 11C
Figure 11E:
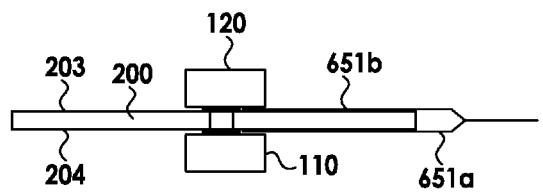
FIG. 11E is a side view of the embodiment of FIG. 11A with the clamping pin and sleeve in place.
Figure 11F:
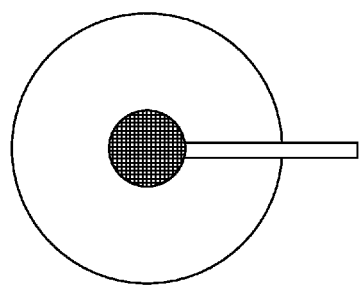
FIG. 11F is a top down view of the embodiment of FIG. 11E.

The portion of the flex circuit (651) around the central hole (201), which is indicated by a square patch in FIGS. 11B and 11D (although it may be any shape), will generally be exposed on only one side so that an electrical contact may be made between that side and the platinum electrode (203) or (204). This can minimize the amount of precious metal used in the flex circuit (651) through the use of various techniques, such as, but not limited to, selective gold plating. The remainder of the flex circuit (651) can be of more conventional materials, such as, but not limited to copper, in order to save on material costs as long as these portions are encapsulated in a material, such as those indicated above, that is resistant to acid. In an embodiment using a flex circuit (651) it is also possible to eliminate the uprights (153).

As shown in the comparison of FIGS. 11A and 11C, the flex circuit (651) may be all one thickness as shown in FIG. 11A where the central patch (451) is the same thickness as the remainder or may be preferentially thicker at the central patch (551) around the central hole (201) to provide more consistent electrical contact. In a still further embodiment, the designs of FIGS. 10 and 11 may be combined with one side of the assembly including a flex circuit (651) and the other side including a wire (150).

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention, and that the invention will include all embodiments falling within the scope of the appended claims.

It will further be understood that any of the ranges, values, or characteristics given for any single component of the present invention can be used interchangeably with any ranges, values, or characteristics given for any of the other components of the invention, where compatible, to form an embodiment having defined values for each of the components, as given herein throughout.

What claimed is:

1. A fuel cell sensor comprising:
a generally flat wafer having:
two opposing major surfaces;
a hole; and
an electrode on each of said two opposing major surfaces said electrode extending to an outer periphery; and
a plurality of elongated wires having a major dimension, each of said wires including:
a base portion; and
an upright;
wherein said base portion is arranged to be all of the following:
non-linear in said major dimension;
generally planar within a perimeter; and
said perimeter being smaller than said outer periphery;
wherein said upright of said first of said plurality of elongated wires extends through said hole and said upright of said plurality of elongated wires is above said hole; and
wherein said upright is generally linear in said major dimension;
wherein said base portion of a first of said plurality of elongated wires is arranged parallel to and in contact with a first of said electrodes; and
wherein said base portion of a second of said plurality of elongated wires is arranged parallel to and in contact with a second of said electrodes.

2. The fuel cell sensor of claim 1 wherein said base portion and said upright are arranged so that said upright is generally orthogonal to the plane of said base portion.

3. The fuel cell sensor of claim 1 further comprising a clamping pin, said clamping pin including: a pin base, said pin base being adjacent to said base portion of said first of said elongated wires; and a column, said column extending through said hole.

4. The fuel cell sensor of claim 3 wherein said column further includes: a first groove through which said upright of said first of said plurality of elongated wires extends; and a second groove through which said upright of said second of said plurality of elongated wires extends.

5. The fuel cell sensor of claim 4 wherein said base further includes a groove corresponding to said base portion of said first of said elongated wires.

6. The fuel cell sensor of claim 5 further comprising a sleeve, said sleeve including a central opening corresponding in size and shape to said column so that said sleeve can fit over said column.

7. The fuel cell sensor of claim 6 wherein said sleeve includes a geometric tab feature, said geometric tab feature mating with the slot on said clamping pin.

8. The fuel cell sensor of claim 3 wherein said hole passes through the center of said electrodes.

9. The fuel cell sensor of claim 8 wherein said fuel cell is enclosed in a housing having an upper portion and a lower portion, said upper portion including a central hole, and both said upright of said first of said plurality of elongated wires and said upright of said second of said plurality of elongated wires extend through said hole in said upper portion.

10. The fuel cell sensor of claim 9 wherein said base portion of said first of said plurality of elongated wires is closer to said lower portion than said upper portion and said base of said second of said plurality of elongated wires is closer to said upper portion than said lower portion.

11. The fuel cell sensor of claim 10 wherein a gas sample is supplied through a gas intake port in said lower portion.

12. The fuel cell sensor of claim 1 wherein said electrodes comprise platinum.

13. The fuel cell sensor of claim 1 wherein said wires comprise platinum.

14. The fuel cell sensor of claim 1 wherein said wires are selected from the group consisting of: round wires and wire ribbons.

* * * * *